United States Patent [19]

Bononi

[11] Patent Number: 5,422,347
[45] Date of Patent: Jun. 6, 1995

US005422347A

[54] β-CYCLODEXTRIN COMPLEXES OF MICONAZOLE AND ECONAZOLE

[75] Inventor: Loris J. Bononi, Gabbiana, Italy

[73] Assignee: Bononi & C. Gruppo di Ricerca S.r.L., Florence, Italy

[21] Appl. No.: 579,084

[22] Filed: Sep. 5, 1990

Related U.S. Application Data

[63] Continuation of Ser. No. 184,297, Apr. 21, 1988, abandoned.

[30] Foreign Application Priority Data

Apr. 24, 1987 [IT] Italy .................... 20256A/87

[51] Int. Cl.$^6$ .................. C08B 37/16; A01N 43/04
[52] U.S. Cl. ........................... 514/58; 536/103
[58] Field of Search ............... 514/58, 396, 858; 536/103

[56] References Cited

U.S. PATENT DOCUMENTS 3,459,731  8/1969  Gramera et al. .............. 536/103
4,764,604  8/1988  Müller ....................... 536/103

FOREIGN PATENT DOCUMENTS 0197571  10/1986  European Pat. Off. ........ 514/103
8502767   7/1988  WIPO ...................... 514/103

OTHER PUBLICATIONS

Van Doorne et al., Proc. 4th Int. Symp. Cyclodextrin Apr. 20–22, 1988, Ed. Huber.
Franko et al., Tag. Ber. Akad. Landwirtsch. Wiss, DDR (1987), 253, 311–314.
Van Doorne et al, Pharm. Weeklad Sci. Ed. 1988, vol. 10, pp. 80–85.

*Primary Examiner*—Irene Marx
*Attorney, Agent, or Firm*—Michael N. Meller

[57] ABSTRACT

The econazole and miconazole complexes with β-cyclodextrin show in vitro a good anti-fungal activity with a wide spectrum and, if locally applied, are well tolerated and more effective than the corresponding nitrates for the control, in vivo and clinically, of mycosis as induced from dermatophytes and from *Candida albicans*.

4 Claims, 8 Drawing Sheets

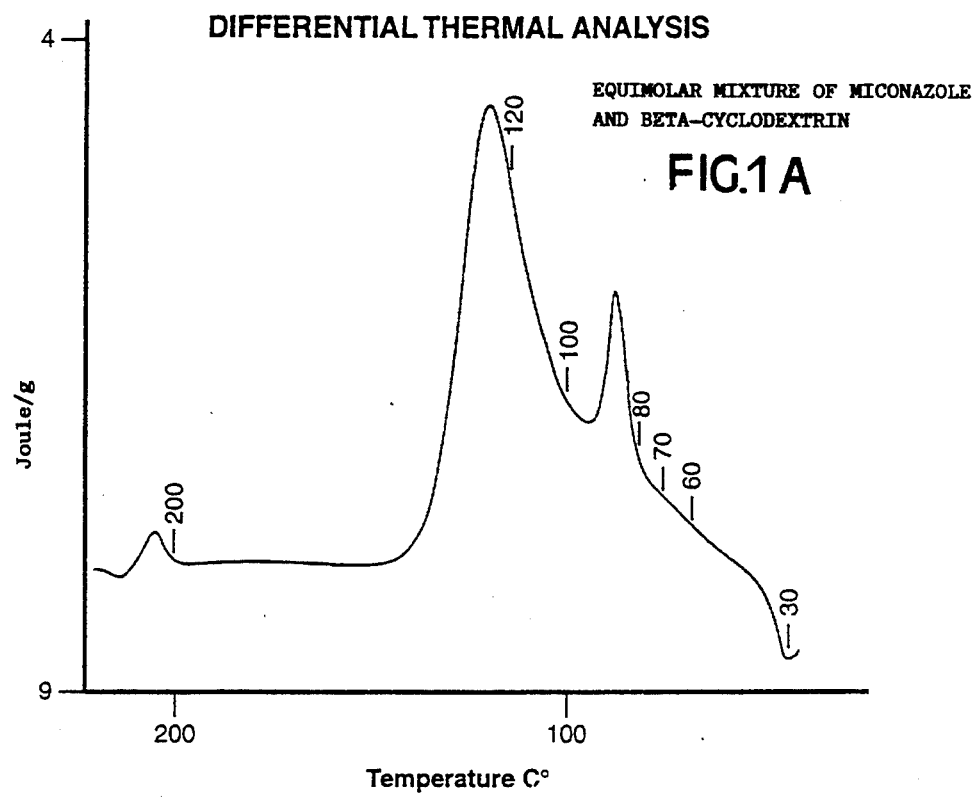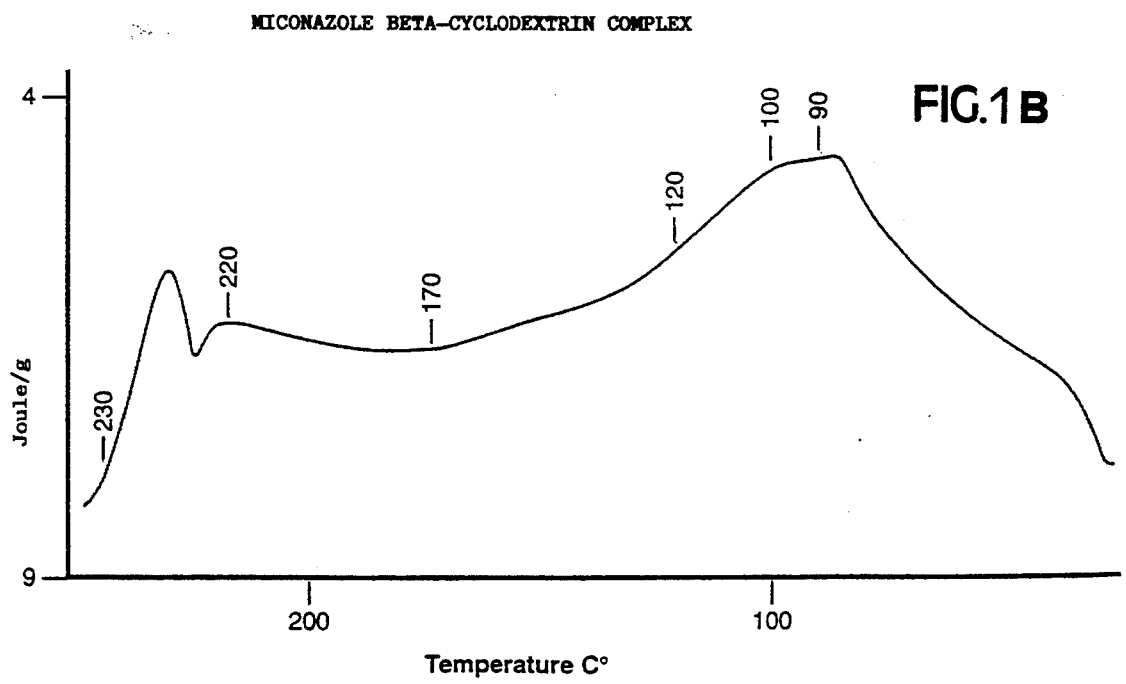

β-CYCLODEXTRIN COMPLEXES OF MICONAZOLE AND ECONAZOLE

This application is a continuation of application Ser. No. 184,297, filed Apr. 21, 1988, now abandoned.

The present invention relates to novel derivatives of miconazole and econazole, more specifically to complexes of these compounds with β-cyclodextrin having, anti-mycotic activity.

The cutaneous mycoses are infections mainly induced from dermatophytes and from *Candida Albicans*. The dermatophytes are fungi found as parasites in the horny layer, in the hair and in the nails owing to the presence of keratolytic enzymes, capable of hydrolyzing the long polypeptidic chains of keratin.

Three genuses (Trichophyton, Microsporum and Epidermophyton) are mainly responsible of the cutaneous pathologies. The infections induced from *dermatophytes* are generally defined as *tinea*. Depending on the part affected there are several clinical pictures: *tinea capiris, tinea barbae, tinea corpotis, tinea cruris, tinea padis, tinea manuum, tinea faciei, tinea unguium*.

The *Candida albicans* is a ubiquitous, non keratinophylic fungus, normally being saprophyte of cutis and of mucosae, which becomes pathogenic when its sprouting and reproduction are promoted by a particularly suitable environment or by the weakening of the organic defenses.

The clinical evidences induced from *Candida albicans* vary according to the part involved: intertriginis, vulvovaginities, oral candidiases ("thrush"), paronichia.

Among the drugs useful for the topical treatment of surface mycosis, is the imidazole derivatives have acquired, in the last years, a relevant importance.

Miconazole, namely 1-(2-( (2,4-dichlorophenyl)-2-(2,4-dichlorophenyl)-methoxy)ethyl)-1-imidazole having formula:

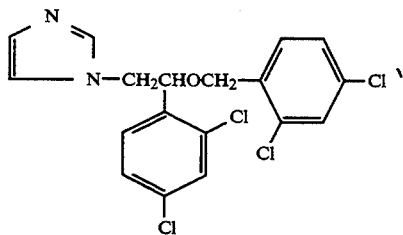

is a compound well known for its anti-mycotic activity. More particularly, miconazole is an anti-mycotic drug with a wide activity spectrum; it is endowed with a powerful activity against dermatophytes and *Candida albicans*, as well as against some Gram-positive gems. The action thereof takes place by selective inhibition of the purine and glutamine fixing onto the membranes of mycetes.

The miconazole is used as the nitrate in several pharmaceutical forms (cream, powder, ovuli, etc.).

In turn econazole, namely 1-(2-((4-chlorophenylmethoxy)-2-(2,4-dichlorophenyl)ethyl)-1H-imidazole having the formula:

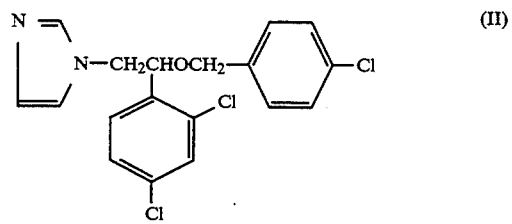

is a compound also known and therapeutically used for the same indications.

Also, this active principle is therapeutical when used as the nitrate.

Lastly, cyclodextrins are a family of natural substances and are prepared through an enzymatic modification of starch to form cyclic units of D-glycopyranose α (1 →P)-linked. Depending on the number of units there are α, β and γ cyclodextrin (respectively comprising 6, 7 and 8 units.

The formula of one unit is the following:

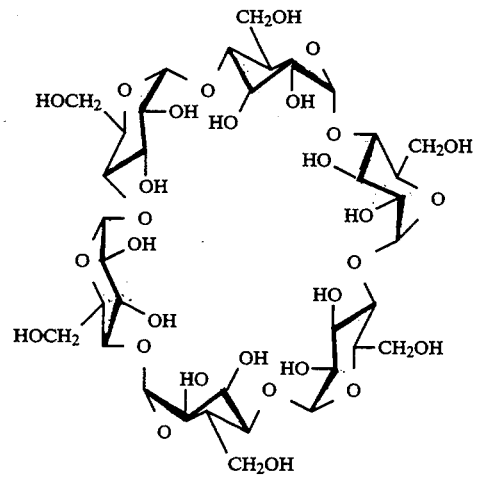

The compounds of the present invention are chemically defined as inclusion complexes, respectively 1-(2-(2,4-dichlorophenyl)-2-((2,4-dichlorophenyl)-methoxy)-ethyl)-1H-imidazole β-cyclodextrin (miconazole -β-cyclodextrin) in the molecular ratio of 1:1 corresponding to the formula $C_{60}H_{84}Cl_4N_2O_{36}$, the molecular weight of which is 1551.12, and 1-(2-((4-chlorophenyl)-methoxy)-2-(2,4-dichlorophenyl)-ethyl)-1H-imidazole β-cyclodextrin (econazole β-cyclodextrin), the molecular ratio of which is 1:1 corresponding to the formula $C_{60}H_{85}C_3N_2O_{36}$, and having molecular weight 1516.36.

The compounds of the invention are in form of a white fine powder, soluble in dimethylsulfoxide, poorly soluble in water, insoluble in methyl and ethyl alcohols and in the common organic solvents.

BRIEF DESCRIPTION OF THE DRAWINGS

FIG. 1A shows the differential thermal analysis of an equimolar mixture of miconazole and β-cyclodextrin.

FIG. 1B shows the differential thermal analysis of the miconazole-β-cyclodextrin complex.

Figure 2A:
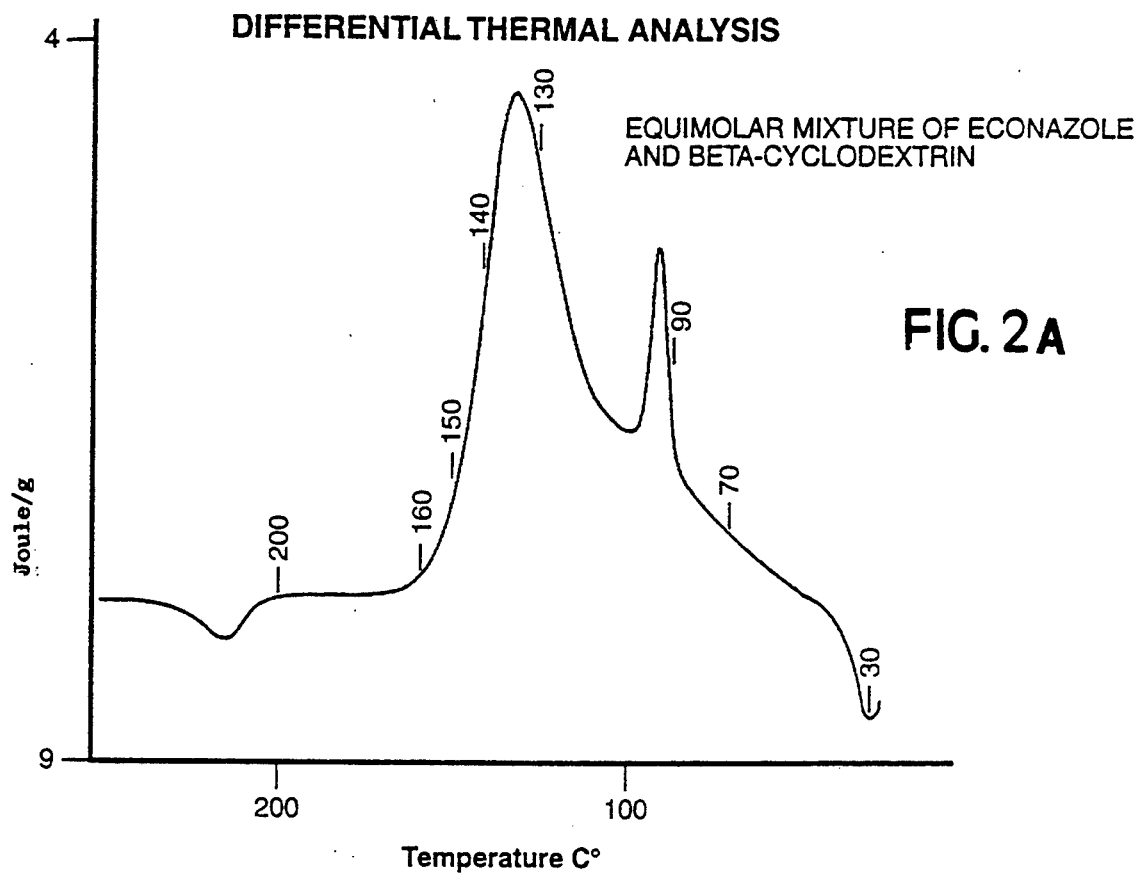
FIG. 2A shows the differential thermal analysis of an equimolar mixture of econazole and β-cyclodextrin.
Figure 2B:
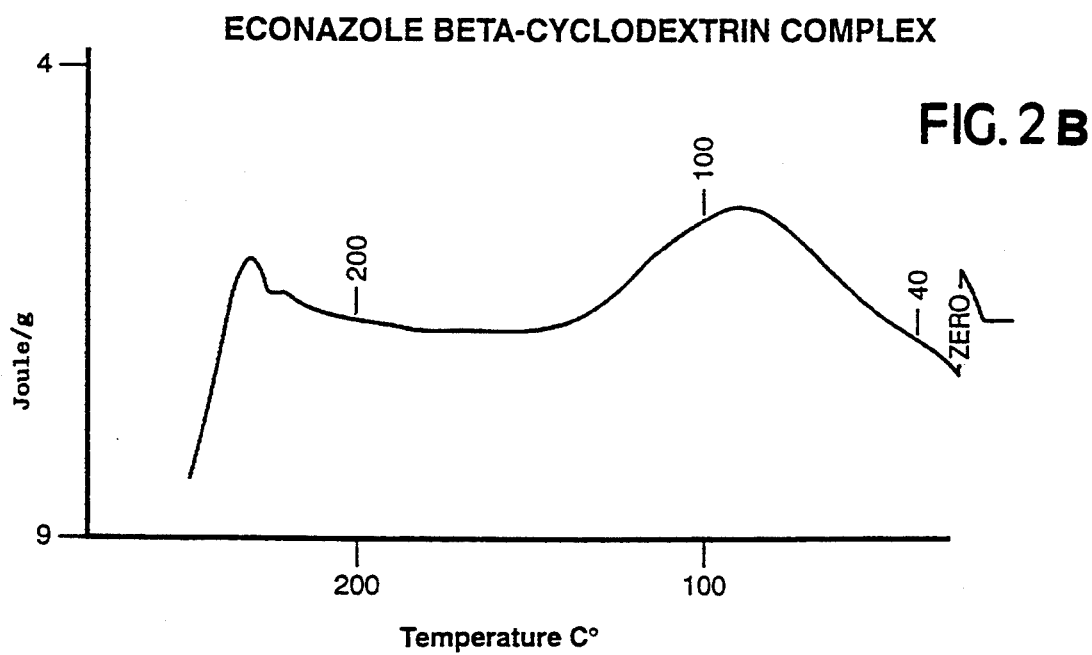
FIG. 2B shows the differential thermal analysis of the econazole-β-cyclodextrin complex.

The differential thermal analysis of the mere physical mixture both of miconazole and of econazole with β-cyclodextrin shows the presence of the endothermal peak of the miconazole and of the econazole at 85° C., whereas in the case of the compounds of the invention the corresponding thermograph is fully different and the disappearance of such a peak is observed (FIGS. 1 and 2).

The saturated aqueous solutions of said compounds have a pH of 3,70 for miconazole β-cyclodextrin and of 3.75 for econazole β-cyclodextrin, as measured with a glass electrode.

The compounds of the invention are prepared by reacting equimolar amounts of miconazole, respectively econazole, with β-cyclodextrin in water and then by lipophylization of the solution. The process shall be better understood from the following examples, given only for illustrative but not limiting purposes.

EXAMPLE 1

4.8 mmoles of miconazole and 4.8 mmoles of β-cyclodextrin are charged in a flask containing 2 liters of bidistilled water and the mixture is stirred by means of magnetic stirrer in a thermostatic bath at 40° C. for 5 days. This solution is then lipophylized by means of an Edwards Minifast Mod. Do. 2 ligostat, by carrying out complete freezing at −35° C., the primary cryoscopic drying at +20° C. under a vacuum of $10^{-1}$ mbar, the secondary one at +30° C. and 10 mbar up to completion. The thus obtained product is then washed with ethyl ether, filtered and dried. Thus, the inclusion complex of miconazole β-cyclodextrin is obtained in quantitative yield.

Figure 3:
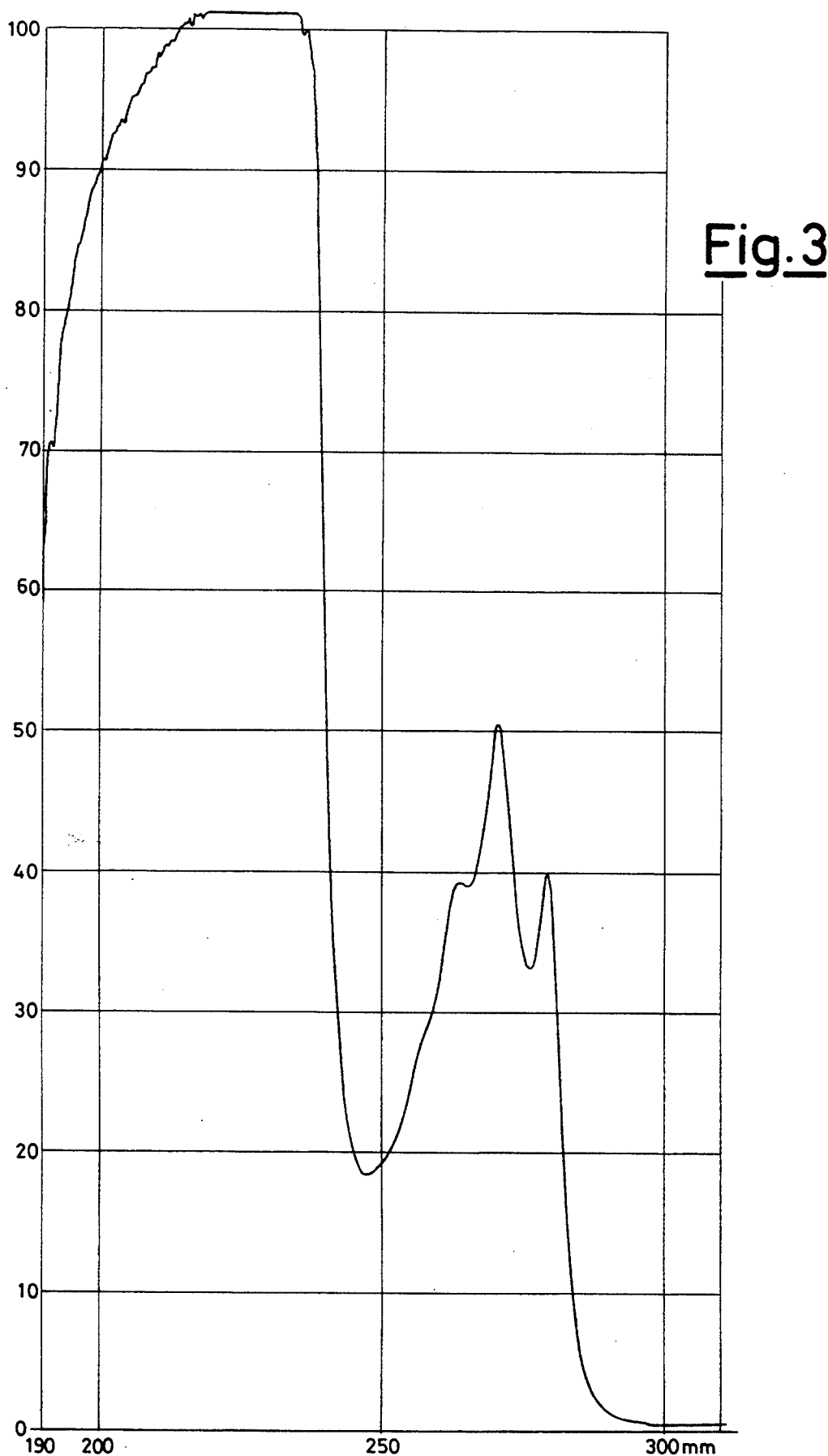
FIG. 3 shows the UV spectrum of miconazole-β-cyclodextrin complex.
Figure 4:
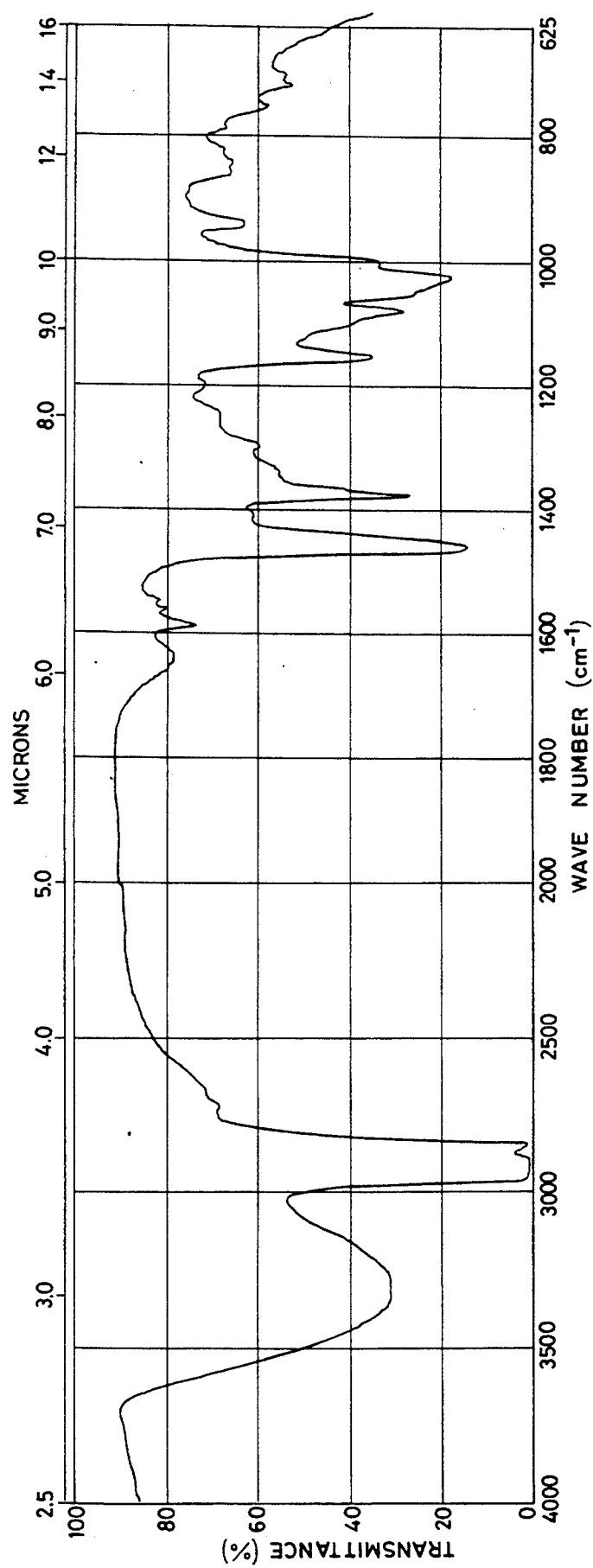
FIG. 4 shows the IR spectrum of miconazole-β-cyclodextrin complex.
Figure 5:
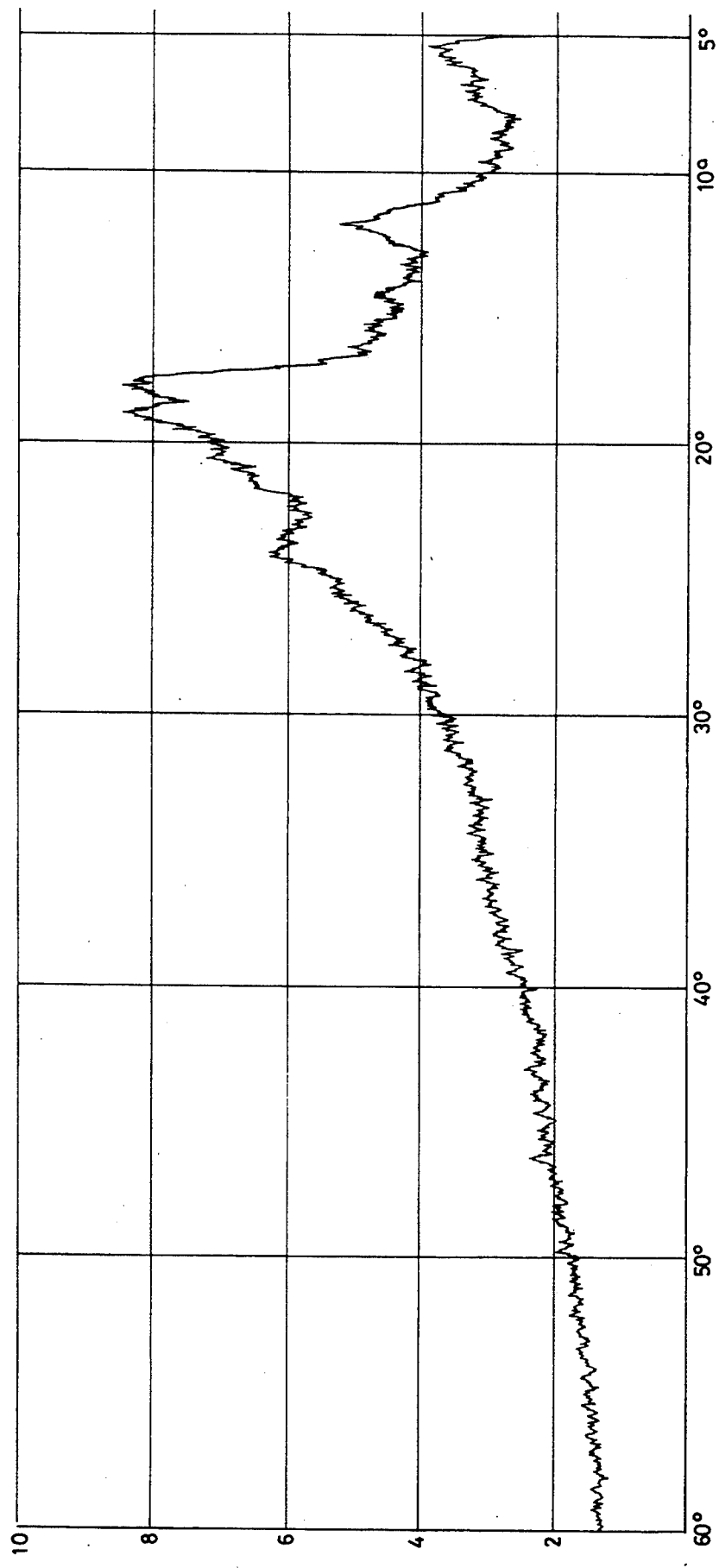
FIG. 5 shows the differential thermal analysis of the miconazole-β-cyclodextrin complex.

The U.V. and I.R. spectra and the differential thermal analysis confirm its formation (see FIGS. 3, 4 and 5).

EXAMPLE 2

5.24 mmoles of econazole and 5.24 mmoles of β-cyclodextrin are charged in a flask containing 2 liters of bidistilled water and the mixture is stirred by means of magnetic stirrer in a thermostatic bath at 40° C. for 5 days. This solution is then lipophylized by means of an Edwards Minifast Mod. Do. 2 lipostat, by carrying out the complete freezing at −35° C., the primary cryoscopic drying at +20° C under a vacuum of $10^{-1}$ mbar, the secondary one at +30° C and $10^{-2}$ mbar up to complete. The thus-obtained product is then washed with ethyl ether, filtered and dried. Thus, the inclusion complex of econazole β-cyclodextrin is obtained in quantitative yield.

Figure 6:
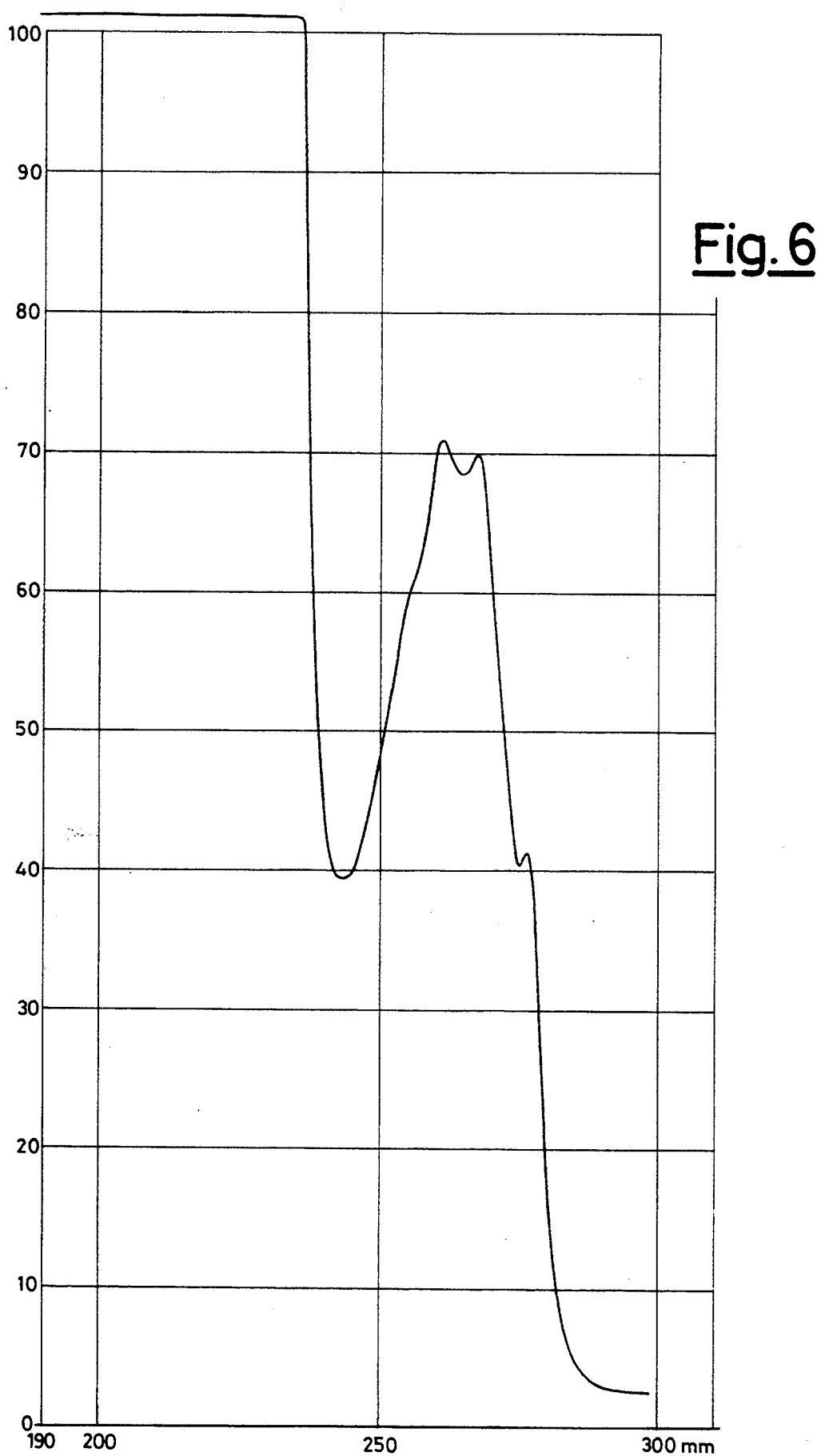
FIG. 6 shows the UV spectrum of econazole-β-cyclodextrin complex.
Figure 7:
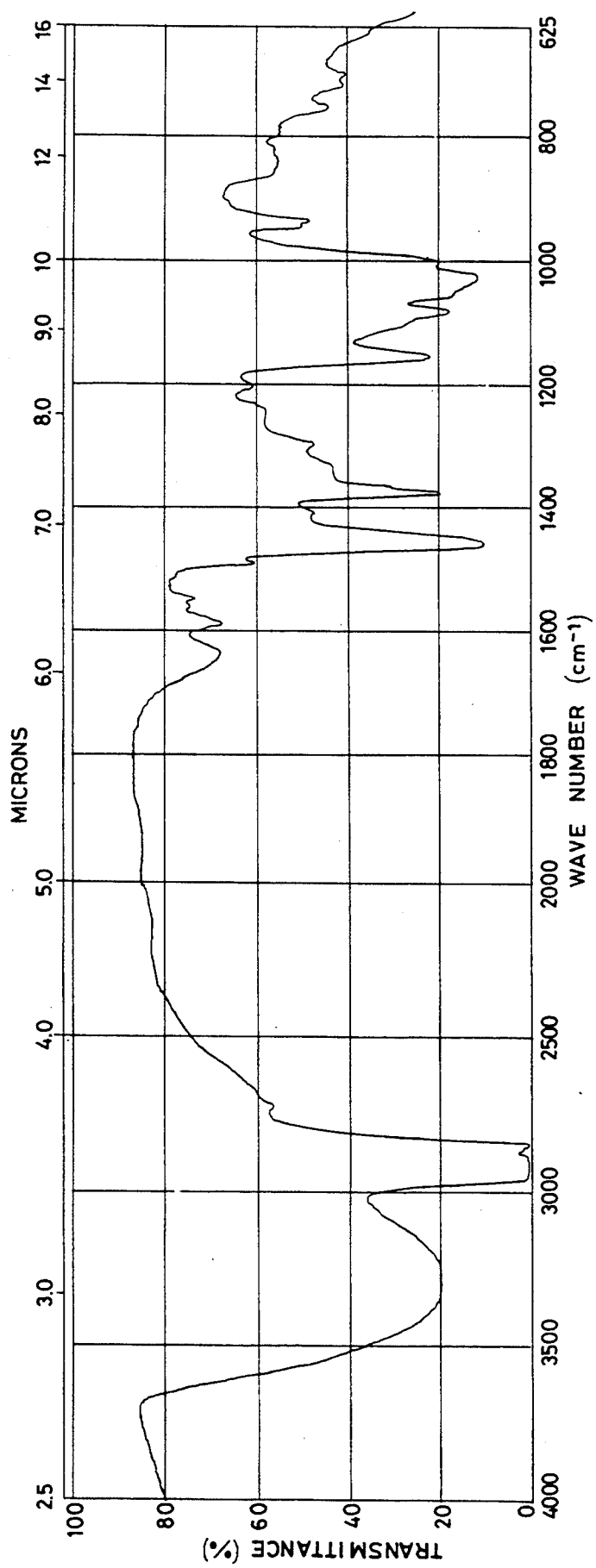
FIG. 7 shows the IR spectrum of econazole-βcyclodextrin complex.
Figure 8:
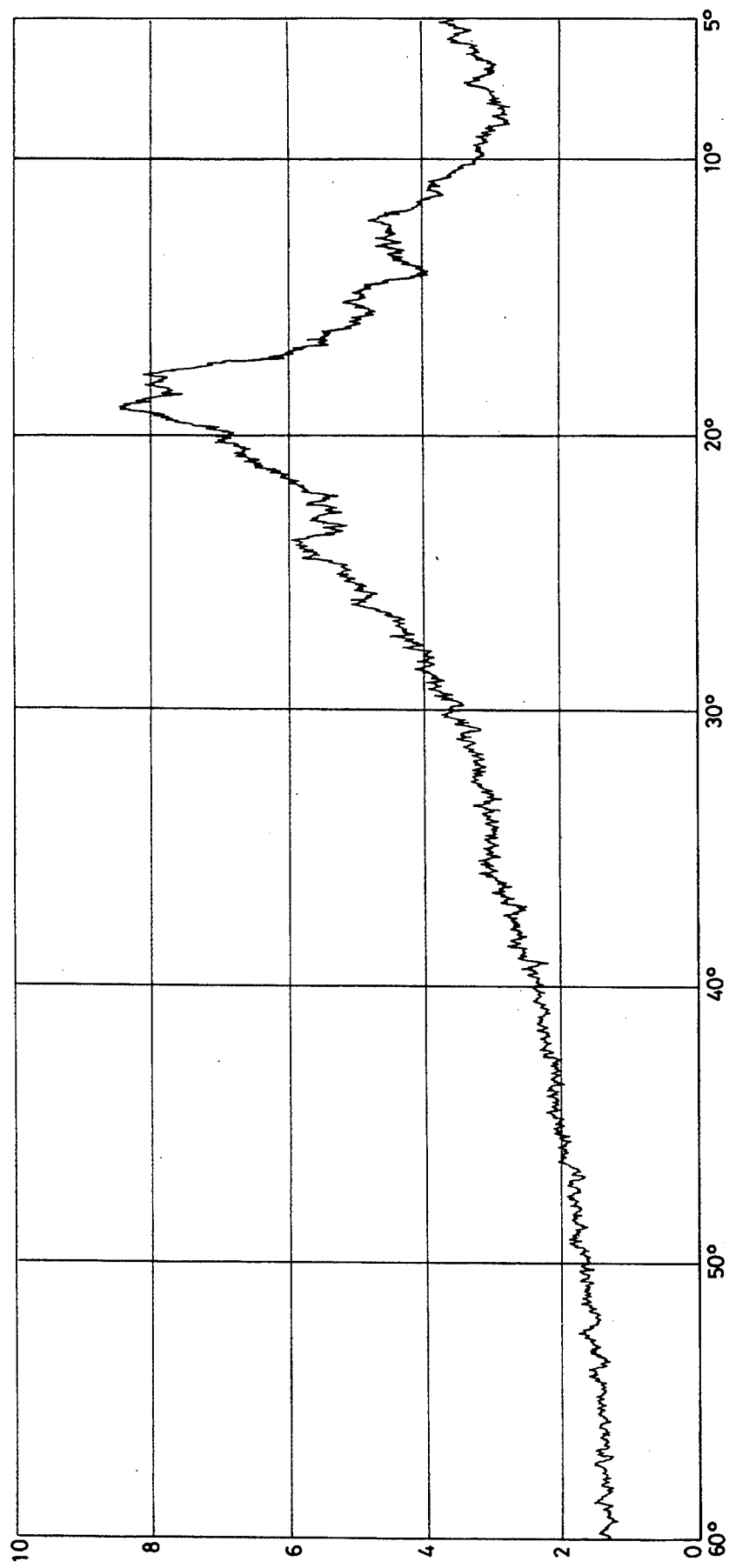
FIG. 8 shows the differential thermal analysis of econazole-β-cyclodextrin complex.

The U.V. and I.R. spectra and the differential thermal analysis confirm its formation (see FIGS. 6, 7 and 8).

In Vitro Antimycotic Activity a) Miconazole β-cyclodextrin

The antimycotic activity of miconazole β-cyclodextrin was evaluated against *Candida albicans* 73/079 (YMA and SAB), *Cryptococcus neoformans* 451, *Sapcharomyces cerevisiae*, *Aspergillus niger*, *Trichophyton mentagrophytes* 569A, *Hendersonula toruloidea* TH65 and *Pacilomyces varioti*.

The microorganisms were incubated in an agar-glucose medium, (Sabourauds medium) at 30° or 37° C., depending on the species, in the presence of miconazole β-cyclodextrin.

The incubation was for 24 hours for Candida and Cryptococcus, and for 48–72 hours for the other mycetes. The miconazole β-cyclodextrin was solubilized in dimethylsulfoxide (DMSO), and then diluted in phosphate buffer at pH 6.6 up to a concentration of 100 ug/ml.

The diameters of the inhibition areas are reported in table 1.

Under these experimental conditions the results indicate a relevant anti-mycotic activity in vitro of miconazole β-cyclodextrin.

TABLE 1

Diameter of the inhibition area for some microorganisms in the presence of miconazole β-cyclodextrin and miconazole nitrate.

| Microorganism | M.B-DXT. mm | M.N. mm |
|---|---|---|
| *Candida Albicans* 73/079 (YMA) | 20.2 | 23.8 |
| *Candida Albicans* 73/079 (SAB) | 16.7 | 20.0 |
| Cryptococcus 451 | 28.3 | 30.4 |
| *Saccharomyces cer.* | 21.6 | 24.9 |
| *Aspergillus niger* | 16.0 | 17.0 |
| Trychopyton 569A | 43.9 | 31.4 |
| *Hendersonula toruloidea* TH65 | 23.4 | 23.1 |

M.B-DXT. = miconazole β-cyclodextrin
M.N. = miconazole nitrate
b) econazole β-cyclodextrin The antimycotic activity of econazole β-cyclodextrin was evaluated against *Candida albicans* 78/079 (YMA and SAB), *Cryptococcus neoformans* 451, *Sapcharomyces cerevisiae*, *Aspergillus niger*, *Trichophyton mentagrophytes* 569A, *Hendersonula toruloidea* TH65 and *Pacilomyces varioti*.

The microorganisms was incubated in a agar-glucose medium, (Sabourauds medium) at 30° or 37° C., depending on the species, in the presence of econazole β-cyclodextrin.

The incubation was for 24 hours for Candida and Cryptococcus, and for 48–72 hours for the other mycetes. The econazole β-cyclodextrin was solubilized in dimethylsulfoxide (DMSO), and then diluted in phosphate buffer at pH 6.6 up to a concentration of 100 ug/ml.

The diameters of the inhibition areas are reported in table 2.

Under these experimental conditions the results indicate a relevant anti-mycotic activity in vitro of econazole β-cyclodextrin.

TABLE 2

Diameter of the inhibition area for some microorganisms in the presence of econazole p-cyclodextrin and econazole nitrate.

| Microorganism | E.B-DXT mm | E.N. |
|---|---|---|
| *Candida Albicans* 73/079 (YMA) | 20.8 | 23.8 |
| *Candida Albicans* 73/079 (SAB) | 21.3 | 20.0 |

TABLE 2-continued

Diameter of the inhibition area for some microorganisms in the presence of econazole β-cyclodextrin and econazole nitrate.

| Microorganism | E.B-DXT mm | E.N. mm |
|---|---|---|
| Cryptococcus 451 | 23.3 | 30.4 |
| Saccharomyces cer. | 24.0 | 24.9 |
| Aspergillus niger | 20.3 | 17.0 |
| Trychopyton 569A | 30.0 | 31.4 |
| Hendersonula toruloidea TH65 | 23.6 | 23.1 |

E.B-DXT. = econazole β-cyclodextrin
E.N. = econazole nitrate

Since for some imidazole derivatives a discrepancy has been detected, sometimes of relevant magnitude, between the antimycotic activity in vitro and that in vivo (Richardson et al., Antimicrob Agents Chemother 27: 832, 1985), and since both the tests of antimycotic activity in vivo and the tests of therapeutical activity in the human being suffering from skin mycosis are considered as more reliable than those in vitro (Odds et al. J. Antimicrob. Chemoter. 18, 473, 1986), the antimycotic activity of miconazole β-cyclodextrin has been determined both in the experimental animals and in human beings.

Antimycotic Activity In Vivo a) Miconazole β-cyclodextrin The antimycotic activity of miconazole β-cyclodextrin has been investigated in vivo in an infection model induced from *Candida albicans* in comparison with miconazole nitrate.

The experiment has been carried out according to the model of Van Cutsem and Thienpont (J. Van Cutsem and D. Thienpont. Experimental cutaneous *Candida Albicans* infections in guinea pigs. Sabouraudia 9:17, 1971).

A group of 40 guinea pigs, previously treated with alloxan, was inoculated with $3 \times 10^6$ astospores and *C. Albicans* in a shaved cutis area. The hair was shaved at beginning of the experiment and, subsequently, every seven days.

Immediately after the inoculation, the animals were divided into four groups: the first group did not received any treatment and was used as the control; the second group was treated with a placebo; the third group was treated with 2% miconazole nitrate cream; the fourth group was treated with 2% miconazole β-cyclodextrin cream. All the treatments were carried out with two cutaneous applications per day at 12 hours interval between them.

The lesion entity was evaluated after 7, 15 and 25 days from the inoculation according to a rating score scale: 0) no lesions; 1) slight lesion; 2) moderate lesion; 3) marked lesion; 4) heavy lesion.

The results are reported in table 3.

The placebo application (cream devoid of the active principle) had no influence on the lesion behaviour, as demonstrated from the possibility of superimposing the scopes of the first group (no treatment) and of the second group of animals (placebo).

On the contrary, relevant slighter lesions and a quick recovery were observed in animals treated in comparison with 2% miconazole nitrate cream, as demonstrated from the lower score recorded fop the third group at each of the three observation times.

Lastly, fop the animals treated with 2% miconazole β-cyclodextrin cream a relevantly faster recovery was observed with respect to the animals treated with 2% miconazole nitrate cream, as demonstrated from the difference of the scores recorded for the third and fourth groups of animals.

The results of the experiments demonstrated that miconazole β-cyclodextrin is endowed with an in vivo anti-mycotic activity higher than that of miconazole nitrate, thus leading to the recovery of the lesion induced from *Candida albicans* in shorter times and in a more efficacious way.

TABLE 3

Antimycotic activity of miconazole β-ciclodextrin in comparison with miconazole nitrate in a cutaneous infection model induced from *Candida Albicans*

| Group | N. of guinea pigs | Lesions scores | | | | |
|---|---|---|---|---|---|---|
| | | 0 | 1 | 2 | 3 | 4 |
| No treatment | 10 | 0 | 0 | 0 | 4 | 6 |
| | | 0 | 0 | 1 | 4 | 5 |
| | | 6 | 0 | 3 | 4 | 3 |
| Placebo | 10 | 0 | 0 | 1 | 4 | 5 |
| | | 0 | 0 | 2 | 5 | 3 |
| | | 0 | 1 | 2 | 4 | 3 |
| Miconazole nitrate 2% | 10 | 1 | 3 | 4 | 2 | 0 |
| | | 2 | 3 | 3 | 3 | 0 |
| | | 5 | 2 | 3 | 0 | 0 |
| Miconazole B-DXT 2% | 10 | 4 | 3 | 3 | 0 | 0 |
| | | 5 | 3 | 2 | 0 | 0 |
| | | 7 | 3 | 0 | 0 | 0 |

Scores of the lesions: 0) absent; 1) slight; 2) moderate; 3) marked; 4) heavy
b - econazole β-cyclodextrin The experimentation was repeated as at the paragraph (a) supra. The results are reported in the table 4.

TABLE 4

Antimycotic activity of econazole β-cyclodextrin in comparison with econazole nitrate in a cutaneous infection model induced *Candida Albicans.*

| Group | N. of guinea pigs | Lesion scores | | | | |
|---|---|---|---|---|---|---|
| | | 0 | 1 | 2 | 3 | 4 |
| No treatment | 10 | 0 | 0 | 0 | 5 | 5 |
| | | 0 | 0 | 1 | 5 | 4 |
| | | 0 | 1 | 2 | 4 | 3 |
| Placebo | 10 | 0 | 0 | 1 | 6 | 3 |
| | | 0 | 0 | 3 | 4 | 3 |
| | | 0 | 1 | 2 | 4 | 3 |
| Econazole nitrate 2% | 10 | 1 | 3 | 3 | 3 | 0 |
| | | 2 | 3 | 3 | 2 | 0 |
| | | 5 | 3 | 2 | 0 | 0 |
| Econazole B-DXT 2% | 10 | 3 | 4 | 3 | 0 | 0 |
| | | 5 | 3 | 2 | 0 | 0 |
| | | 8 | 2 | 0 | 0 | 0 |

Scores of the lesions: 0) absent; 1) slight; 2) moderate; 3) marked; 4) heavy.

In this case, too, the placebo application (cream devoid of the active principle) had no influence on the lesion behaviour, as demonstrated from the possibility of superimposing the scores of the first group (no treatment) and of the second group of animals (placebo).

On the contrary, relevant slighter lesions and a quick recovery were observed in animals treated in comparison with 2% econazole nitrate cream, as demonstrated from the lower score recorded for the third group at each of the three observations times.

Lastly, for the animals treated with 2% econazole β-cyclodextrin cream a relevantly faster recovery was observed with respect to the animals treated with 2% econazole nitrate cream, as demonstrated by the difference of the scores recorded for the third and fourth groups of animals.

The results of the experiments demonstrated that econazole β-cyclodextrin is endowed with an in vivo anti-mycotic activity higher than that of miconazole nitrate, thus leading to the recovery of the lesion induced from *Candida albicans* in shorter times and in a more efficacious way.

Antimycotic Activity in the Human Being a) miconazole β-cyclodextrin

The antimycotic activity of miconazole β-cyclodextrin in the human being has been evaluated in comparison with miconazole nitrate in the case of 20 patients suffering from vulvovaginalis candidiasis, diagnostically assessed by means of cultural and microscopical examination.

The patients were randomized and treated, 20 with miconazole nitrate and 20 with miconazole β-cyclodextrin, in form of vaginal ovuli, each containing the equivalent of 100 mg of miconazole base. The posology was of 2 ovuli per day for 14 days. The cultural and microscopic examinations have been repeated after 7 and 14 days from the beginning of the treatment and the results were recorded and reported in table 5.

TABLE 5

Antimycotic activity of miconazole β-cyclodextrin and miconazole nitrate in women suffering from vulvovaginalis candidiasis.

a) Percentage of positivity at culture examination for *Candida albicans*

| | Treatment days | | |
|---|---|---|---|
| | 0 | 7 | 14 |
| Miconazole nitrate | 100 | 40 | 20 |
| Miconazole B-DXT | 100 | 10 | 0 | b) Percentage of positivity at microscopical examination for *Candida albicans*

| | Treatment days | | |
|---|---|---|---|
| | 0 | 7 | 14 |
| Miconazole nitrate | 100 | 40 | 20 |
| Miconazole B-DXT | 100 | 10 | 0 |

From the results of clinical experiments a greater therapeutical effectiveness of the miconazole β-cyclodextrin with respect to the miconazole nitrate is shown as evidenced from the percentages of positivity at the culture examination (10 vs 40% at the seventh day; 0 vs 20% at 14° day (p<0.01) and at the microscopical examination for *Candida Albicans* (10 vs 40% at 7° days; 0 vs 20% at 14° days) (p<0.01).

b) econazole β-cyclodextrin

The experimentation A was repeated as in the previous paragraph (a). The results are reported in Table 6.

TABLE 6

Antimycotic activity of miconazole β-cyclodextrin and econazole nitrate in women suffering from vulvovaginalis candidiasis.

a) Percentage of positivity at culture examination for *Candida albicans*

| | Treatment days | | |
|---|---|---|---|
| | 0 | 7 | 14 |
| Econazole nitrate | 100 | 35 | 15 |
| Econazole B-DXT | 100 | 10 | 0 | b) Percentage of positivity at microscopical examination for *Candida albicans*

| | Treatment days | | |
|---|---|---|---|
| | 0 | 7 | 14 |
| Econazole nitrate | 100 | 35 | 15 |
| Econazole B-DXT | 100 | 10 | 0 |

From the results of clinical experiments a greater therapeutical effectiveness of the econazole β-cyclodextrin with respect to the econazole nitrate is shown as evidenced from the percentages of positivity at the culture examination (10 vs 35% at the seventh day; 0 vs 15% at 14° day (p<0.01).

The compounds of the present invention are used for the preparation of pharmaceutical forms suitable for the topical use and thus for the foreseen therapeutical application, such as creams, ointments, lotions gels, milk, tinctures, powders, ovuli, foams, vaginal capsules, vaginal washings, oral gels.

For their preparation the normal excipients, solvents, vehicles and additives are used, according to the standard pharmaceutical techniques. As regards the dosage of the active principle in the aforesaid pharmaceutical formulations and as regards the use posology, the dosage and posology already known and used for the corresponding nitrates still holds true.

I claim:

1. A complex of beta-cyclodextrin with a compound selected from the group consisting of miconazole and econazole.

2. A pharmaceutical composition comprising, as the active ingredient, an antimycotic effective amount of a complex according to claim 1, together with pharmaceutical excipients.

3. A pharmaceutical composition according to claim 2, in the form suitable for topical application.

4. A complex according to claim 1, wherein the beta-cyclodextrin and, respectively, econazole or miconazole are present in a molecular ration of 1:1.

* * * * *